US00PP23317P2

(12) United States Plant Patent
Pan

(10) Patent No.: US PP23,317 P2
(45) Date of Patent: Jan. 8, 2013

(54) ***LANTANA* PLANT NAMED 'LANZ0002'**

(50) Latin Name: ***Lantana camara* L.**
Varietal Denomination: LANZ0002

(75) Inventor: Shifeng Pan, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/317,045

(22) Filed: Oct. 7, 2011

(51) Int. Cl.
*A01H 5/00* (2006.01)

(52) U.S. Cl. ..... Plt./227

(58) Field of Classification Search ..... Plt./227
See application file for complete search history.

*Primary Examiner* — Annette Para
(74) *Attorney, Agent, or Firm* — Joshua L. Price

(57) ABSTRACT

A new *Lantana* plant named 'LANZ0002' particularly distinguished by the large sized, yellow flowers that mature to orange and light red colored flowers, with excellent floriferousness as a result of limited seed set, and a relatively compact and mounding habit that is well branched with medium green foliage.

1 Drawing Sheet

Latin name of the genus and species of the plant claimed: *Lantana camara* L.

Varietal denomination: 'LANZ0002'.

BACKGROUND OF THE NEW PLANT

The present invention comprises a new *Lantana*, botanically known as *Lantana camara* L., and hereinafter referred to by the variety name 'LANZ0002'.

'LANZ0002' is a product of a planned breeding program. The new cultivar has large sized, yellow flowers that mature to orange and light red colored flowers, with excellent floriferousness as a result of limited seed set, and a relatively compact and mounding habit that is well branched with medium green foliage.

'LANZ0002' originates from a hybridization made in July 2007 in a controlled breeding program in Gilroy, Calif. USA. The female parent was an unpatented, proprietary plant identified as 'G307-1' with peach color, with smaller flower size, fewer inflorescences, and is later to flower.

The male parent of 'LANZ0002' was an unpatented, proprietary plant identified as 'G292-1' with peach color, smaller flower size, more open plant habit and has lighter flower color. The resultant seed was sown in December 2007.

'LANZ0002' was selected as one flowering plant within the progeny of the stated cross in April 2008 in a controlled environment in Gilroy, Calif.

The first act of asexual reproduction of 'LANZ0002' was accomplished when vegetative cuttings were propagated from the initial selection in the April 2008 in a controlled environment in Gilroy, Calif.

BRIEF SUMMARY OF INVENTION

Horticultural examination of plants grown from cuttings of the plant initiated in April 2008 in Gilroy, Calif., and continuing thereafter, has demonstrated that the combination of characteristics as herein disclosed for 'LANZ0002' are firmly fixed and are retained through successive generations of asexual reproduction.

'LANZ0002' has not been observed under all possible environmental conditions. The phenotype may vary significantly with variations in environment such as temperature, light intensity and day length.

A Plant Breeder's Right for this cultivar was applied for in Canada on Dec. 17, 2010, #10-7125. 'LANZ0002' has not been made publicly available more than one year prior to the filing of this application.

The following traits have been repeatedly observed and are determined to be basic characteristics of the new variety. The combination of these characteristics distinguishes this *Lantana* as a new and distinct variety.

BRIEF DESCRIPTION OF THE PHOTOGRAPHS

The accompanying photographic drawing shows typical flower and foliage characteristics of 'LANZ0002' with colors being as true as possible with an illustration of this type. The photographic drawing shows a flowering plant of the new variety, and a close-up of the flowers.

DETAILED BOTANICAL DESCRIPTION

The plant descriptions, measurements and aforementioned photographs were taken in Gilroy, Calif. in April 2011 in a greenhouse. These plants were growing in 4.5 inch pots in a trial setting. The plants were about 12 weeks of age and were grown with several early sprays of Paclobutrazol, a plant growth regular.

Color Chart used: Royal Horticultural Society Colour Chart (R.H.S.) 2001

TABLE 1

DIFFERENCES BETWEEN THE NEW VARIETY 'LANZ0002' AND A SIMILAR VARIETY

| | 'LANZ0002' | 'Balandimpea' (U.S. Plant Pat. No. 19,358) |
|---|---|---|
| Plant habit: | More compact and bushy | Less compact |
| Floriferiousness: | More | Less |
| Flower size: | Larger | Smaller |

Plant:
- *Form, growth and habit*.—Flat, trailing habit that is well branched, apical pinching enhances the number of branches and results in a tighter plant habit.
- *Plant height*.—About 18.0 cm.
- *Plant height* (*inflorescence included*).—About 22.0 cm.
- *Plant width*.—37.0-44.0 cm.

Foliage:
- *Type*.—Opposite.
- *Immature, leaf color, upper surface*.—RHS 137A.
- *Lower surface*.—RHS 137C.
- *Mature, leaf color, upper surface*.—RHS 137A but deeper green.
- *Lower surface*.—RHS 137C.
- *Length*.—6.7-7.1 cm.
- *Width*.—3.9-4.5 cm.
- *Shape*.—Ovate.
- *Base shape*.—Attenuate.
- *Apex shape*.—Acute.
- *Margin*.—Serrulate.
- *Texture, upper*.—Hirsute.
- *Lower surface*.—Hirsute.
- *Color of veins, upper surface*.—Between RHS 144A and RHS 144B.
- *Color of veins, lower surface*.—Between RHS 144A and RHS 144B.
- *Petioles color*.—RHS 144B.
- *Petioles length*.—1.6-2.0 cm.
- *Diameter of petiole*.—0.15 cm.
- *Texture*.—Hirsute; pilose; glandular hairs.

Stem:
- *Quantity of main stems*.—5-6.
- *Color of stem*.—Between RHS 144A and RHS 144B.
- *Length of stem*.—16.0-19.0 cm.
- *Diameter*.—0.3 cm.
- *Length of internodes*.—2.0-4.5 cm.
- *Texture*.—Hirsute; pilose; glandular hairs.

Inflorescence:
- *Type*.—Umbel like, flattened semi-sphere the florets are sessile on an ovate receptacle.
- *Blooming habit*.—Flowers continuously from spring through fall.
- *Number of open flowers per inflorescence*.—20-25 with numerous buds.
- *Quantity of inflorescences per plant*.—About 15.
- *Lastingness of individual blooms on the plant*.—About 4 weeks (depending on temperatures).
- *Fragrance*.—Slightly spicy.
- *Umbel horizontal diameter*.—3.9-4.4 cm.
- *Umbel depth*.—2.0 cm.
- *Peduncle color*.—RHS 144A.
- *Length of peduncle*.—4.0-6.0 cm.
- *Peduncle diameter*.—0.15 cm.
- *Texture*.—Pilose; hirsute; glandular hairs.

Corolla:
- *Floret form*.—Salver-shaped to shallow cup-shaped and zygomorphic, with a relatively long tube at the base. Each flower subtended by a single bract.
- *Floret horizontal diameter*.—1.1 cm.
- *Floret depth*.—1.9-2.1 cm.
- *Immature, color of petals, upper surface*.—RHS 7C with RHS 4A margins and RHS 13A at the corolla opening.
- *Lower surface*.—RHS 4D overlaid with varying shades of RHS 51C on the upper portion.
- *Mature, color petals, upper surface*.—RHS 7A heavily overlaid with shades of RHS N25A to RHS N25C with margins of varying shades of between RHS 51A and RHS 51C.
- *Lower surface*.—RHS 4D overlaid with varying shades of RHS 51C on the upper portion.
- *Petal length*.—0.5-0.6 cm.
- *Petal diameter*.—0.6-0.7 cm.
- *Apex shape*.—Mucronulate.
- *Margin*.—Entire.
- *Shape*.—Obovate.
- *Degree of lobation*.—Moderate.
- *Texture, upper surface*.—Papillose.
- *Lower surface*.—Papillose.
- *Corolla tube, color, outer surface*.—RHS 8D with hint of RHS 8C on under surface; and the upper portion is overlaid with shades of between RHS 50C and RHS 54C.
- *Color, inner surface*.—RHS 2D.
- *Corolla tube length*.—1.3 cm.
- *Diameter* (*at opening*).—0.2 cm.
- *Corolla tube texture, outer surface*.—Pubescent.
- *Inner surface*.—Glabrous.

Bud (just before opening):
- *Color*.—Closest to RHS 36A.
- *Length*.—1.1-1.3 cm.
- *Width*.—0.3 cm.
- *Shape*.—Tubular.

Bract:
- *Color*.—RHS 138A with a slightly darker apex.
- *Length*.—0.6-0.8 cm.
- *Diameter*.—0.2-0.3 cm.
- *Shape*.—Obtuse.
- *Apex shape*.—Acute.
- *Texture, upper surface*.—Glabrous.
- *Lower surface*.—Pubescent.

Calyx:
- *Number of sepals*.—5, fused sepals forming a short tube around the base of each floret.
- *Color of sepals*.—Closest to RHS 138B.
- *Length of sepals*.—0.3 cm.
- *Width of sepals*.—0.2 cm.
- *Apex shape*.—Slightly acute, but some are irregulary and deeply emarginate.
- *Texture, outer surface*.—Pubescent.
- *Inner surface*.—Glabrous.

Reproductive organs:
- *Pistil*.—1.
- *Length*.—0.4 cm.
- *Style color*.—RHS 150D but more translucent.
- *Style length*.—0.35 cm.
- *Stigma color*.—RHS 149D but more green.
- *Stamens*.—4.
- *Color of filaments*.—RHS 150D.
- *Length filaments*.—Approximately 1.0 cm.
- *Anther color*.—RHS 5B.
- *Length of anthers*.—0.1 cm.
- *Pollen amount*.—None was really observed.
- *Color of pollen*.—Not observed.
- *Fertility/seed set*.—Has not been observed on this hybrid.

Disease/pest resistance: Disease/pest resistance has not been observed on this hybrid.

What is claimed is:

1. A new and distinct variety of *Lantana* plant named 'LANZ0002' substantially as illustrated and described herein.

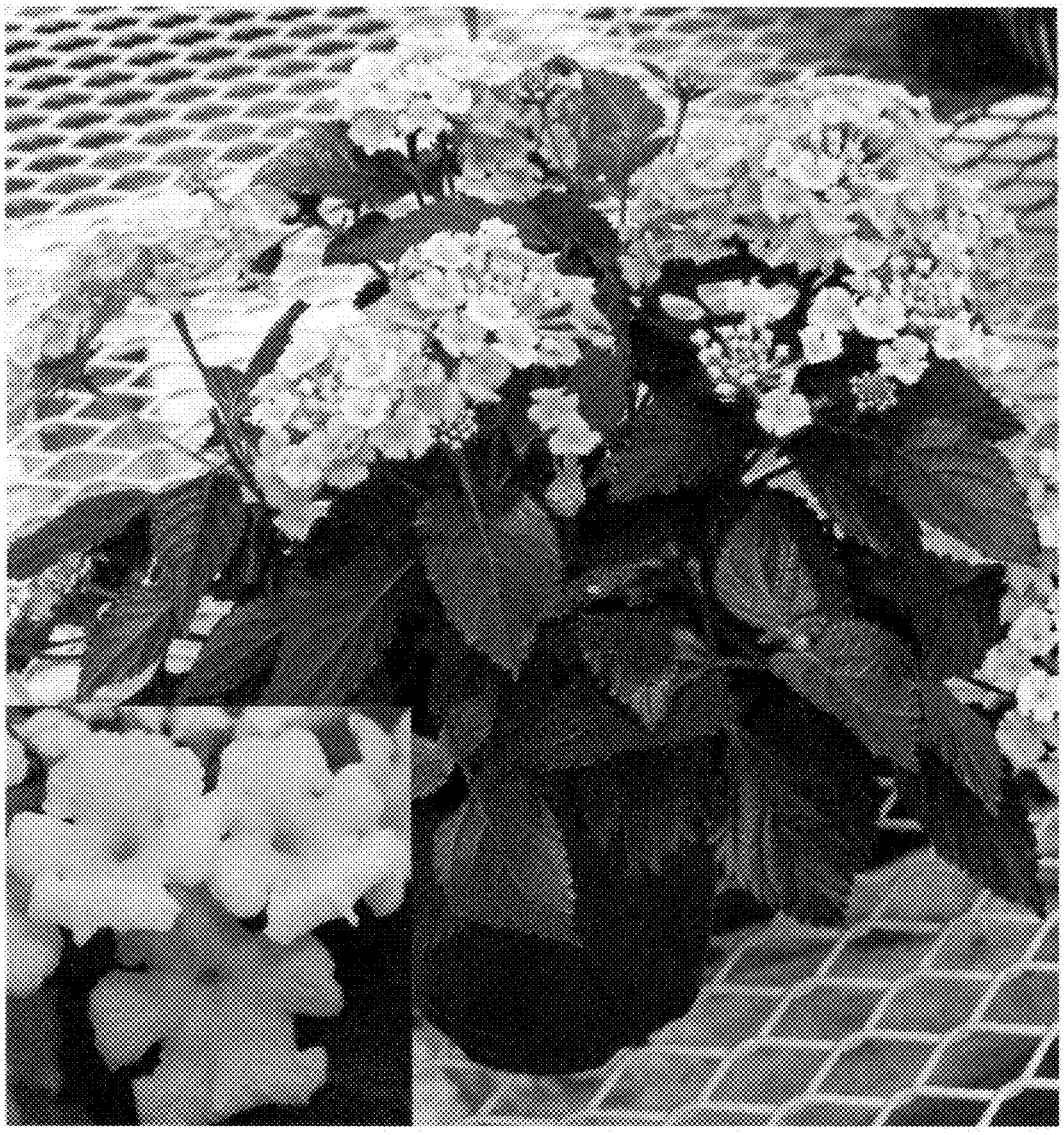

* * * * *